United States Patent [19]

Harrison et al.

[11] Patent Number: 4,741,339
[45] Date of Patent: May 3, 1988

[54] POWER TRANSFER FOR IMPLANTED PROSTHESES

[75] Inventors: James M. Harrison, Watsonia; Peter M. Seligman, Essendon, both of Australia

[73] Assignees: Cochlear Pty. Limited, New South Wales; University of Melbourne, Victoria, both of Australia

[21] Appl. No.: 789,874

[22] Filed: Oct. 21, 1985

[30] Foreign Application Priority Data

Oct. 22, 1984 [AU] Australia ............................ P67767

[51] Int. Cl.$^4$ ............................................. A61N 1/36
[52] U.S. Cl. ............................ 128/419 PS; 128/420.5; 128/903
[58] Field of Search ......... 128/419 PS, 419 R, 419 C, 128/419 E, 419 P, 419 PG, 419 PT, 422, 903, 420.5, 420.6

[56] References Cited

U.S. PATENT DOCUMENTS

| 2,656,839 | 10/1953 | Howard | 128/422 |
| 3,195,548 | 7/1965 | Waller | 128/419 PG |
| 4,014,346 | 3/1977 | Brownlee et al. | 128/419 PS |
| 4,071,032 | 1/1978 | Schulman | 128/419 P |
| 4,441,210 | 4/1984 | Hochman et al. | 128/419 R |
| 4,562,840 | 1/1986 | Batina et al. | 128/419 PT |

Primary Examiner—William E. Kamm
Attorney, Agent, or Firm—Walter J. Madden, Jr.; Alan H. MacPherson

[57] ABSTRACT

Apparatus is provided for improving the coupling between an external inductive transmitting coil and an internal inductive receiving coil to transmit power and/or data to the receiving coil from the transmitting coil. The structure includes a coupling coil inductively coupled to the transmitting coil to increase the Q factor and hence the energy transfer between the transmitting coil and the receiving coil.

6 Claims, 1 Drawing Sheet

POWER TRANSFER FOR IMPLANTED PROSTHESES

CROSS-REFERENCE TO RELATED APPLICATIONS

Copending application Ser. No. 438,806, filed Apr. 11, 1983, now U.S. Pat. No. 4,532,930, and assigned to the same assignee as the present application, describes a cochlear implant system for an auditory prosthesis, and the present invention is useful in practicing the invention taught in that application. The subject matter of that application is hereby incorporated herein by reference.

BACKGROUND OF THE INVENTION

1. Field of the Invention

The invention described herein is primarily for use with a cochlear prosthesis, or implantable hearing prosthesis system, or bionic ear. That is, a system of components designed with the object of restoring some sensations of hearing to the profoundly deaf. The main object of such a system is to improve speech communication, but the importance of awareness of environmental sound is also a factor to be considered.

2. Prior Art

There has been extensive activity in efforts to provide useful hearing through electrical stimulation of auditory nerve fibers, using electrodes placed inside or adjacent to some part of the cochlear structure. Systems using a single pair of electrodes have been proposed in U.S. Pat. Nos. 3,751,605, Michelson and 3,752,939, Bartz. In each of these systems an external speech processing units converts the acoustic input into a signal suitable for transmission through the skin to an implanted receiver/-stimulator unit. These devices apply a continuously varying stimulus to the pair of electrodes, stimulating at least part of the population of auditory nerve fibers, and thus producing a hearing sensation.

An alternative approach has been to utilize the tonotopic organization of the cochlea to stimulate groups of nerve fibers depending on the frequency spectrum of the acoustic signal. Systems using this technique are shown in U.S. Pat. Nos. 4,207,441, Ricard; 3,449,753, Doyle; and 4,063,048, Kissiah.

SUMMARY OF THE INVENTION

The present invention is directed to improving the electromagnetic coupling between a transmitting coil located externally and a receiver coil which is implanted, usually by subcutaneous implantion, in a human body as a part of an implanted hearing prosthesis system. A radio frequency induction link of this type is depicted in FIG. 1, showing a transmitting coil 11, a power and/or data supply 12 and an implanted receiver 13 which is coupled to transmitting coil 11 through a cutaneous layer 15 by an implanted receiving coil 14. The power transfer efficiency of this link is related both to the coupling coefficient, k between the coils 11, 14 and the product of their Q or quality factors. Thus, any mechanism to increase either or both of these two parameters will result in a higher energy transfer efficiency.

In its broadest form, the present invention provides a system for electromagnetically transferring power and/or data comprising a primary transmitter circuit adapted to transfer power and/or data to a secondary receiver circuit, and a tertiary circuit electromagnetically coupled with the primary circuit and tuned to increase the effective Q of the transmitter circuit. The primary transmitter circuit preferably includes a coil which is adapted to be inductively coupled with the secondary receiving circuit. The system also includes a tertiary circuit including a tuned coil which is loosely coupled with the primary coil. The primary and secondary coils are preferably located in close proximity to each other to achieve the necessary inductive coupling.

In an alternative embodiment, the tertiary coil may be positioned closely adjacent to the secondary coil while still being loosely coupled with the primary coil.

More specifically, the present invention provides an improvement in an auditory prosthesis including at least one external coil electromagnetically coupled to at least one internal coil for the purposes of transmitting power and/or information through the skin, the improvement comprising at least one tertiary tuned coil located adjacent to and electromagnetically coupled to the external and internal coils.

DESCRIPTION OF THE PREFERRED EMBODIMENT

Figure 1:
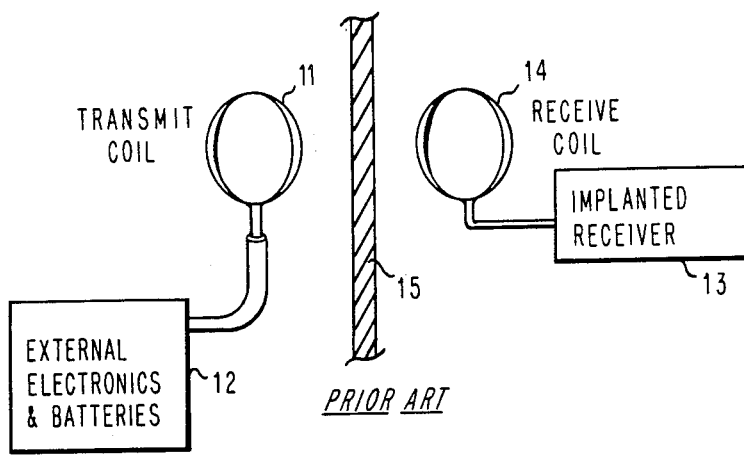
FIG. 1 is a representation of a basic prior art system employing coupling between an external primary or transmitting coil and an implanted secondary or receiving coil.
Figure 2:
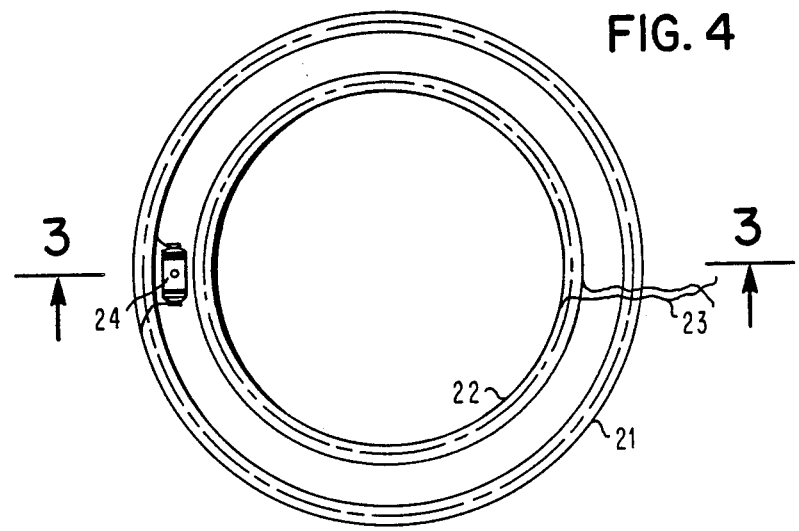
FIGS. 2 and 3 illustrate one embodiment of structure in accordance with the present invention in which the tertiary coil is disposed around the external primary coil.
Figure 3:
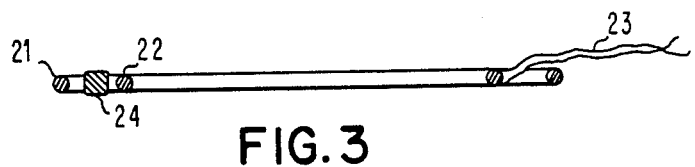

FIGS. 2 and 3 illustrate one embodiment of the present invention in which a tertiary coil 21 is disposed around a primary coil 22. Primary coil 22 is connected by means represented by wires 23 to power supply means and microphone structure, represented by element 12 in FIG. 1, for providing power and/or data to coil 22 for transmission to the secondary or receiving coil represented as 14 in FIG. 1. Preferably, a tuning capacitor having a capacitance C is provided in the electrical path represented by wires 23 to provide for tuning of the LC circuit including the inductance L of the primary coil. Tertiary coil 21, disposed around coil 22, preferably has connected thereto a capacitor 24 whose capacitance may be represented as C' to form an LC circuit including the inductance L' of coil 21.

Figure 4:
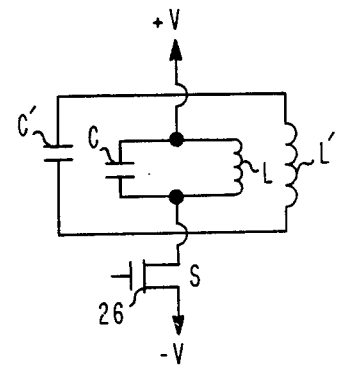
FIG. 4 is an electrical equivalent circuit illustrating the effective electrical parameters involved when using one embodiment of the present invention.

FIG. 4 shows the equivalent electrical circuit for the structure of FIGS. 2 and 3 with the two inductive-capacitive circuits represented by LC and L'C'. FIG. 4 shows a transistor switch 26 as a schematic indication of means for supplying power and data to primary coil 22.

It has been found that by placing the loosely coupled, tuned tertiary coil 21 near the primary coil, as physically shown in FIGS. 2 and 3 and electronically represented in FIG. 4, the effective Q of the transmitter circuit (modeled as a lumped linear circuit) is increased with resultant increase in transfer efficiency.

In a representative, but not limiting, embodiment, the following values were used for the listed electrical and mechanical parameters of the primary and tertiary circuits.

Primary Coil inductance L—3.6 michrohenries

Primary Coil tuning capacitance C—368 picofarads
Tertiary Coil inductance L'—40 microhenries
Tertiary Coil tuning capacitance C'—70 picofarads
Primary Coil diameter—24 millimeters
Tertiary Coil diameter—32 millimeters As an alternative to disposing the tertiary coil outside the primary coil as shown in FIGS. 2 and 3, it may be desirable to mount the tertiary coil inside the primary coil. This may result in a slight reduction in the efficiency of power transfer, but it has the advantage of producing a physically smaller coil assembly.

One measure of clinical importance in evaluating the performance of devices of the type described herein is the maximum range between the transmitting assembly and the implanted receiving assembly at which a usable output is obtained from the implant before a voltage level detector in the implant inhibits output. It has been determined that structure in accordance with the present invention has an effective range of 10.5 millimeters, as compared to a range of 5.5 millimeters for a transmitting coil not employing a tertiary coil as taught herein. It has been discovered that it is not necessary for the tertiary coil to be coaxial, or coplanar with the other coils, but merely inductively coupled with it.

It will be apparent to those skilled in the art that this invention has application in areas other than cochlear prostheses, such as visual prostheses, cerebellar stimulators, pair control devices etc., or any implanted electronic device where it is required to couple power through the skin. The improvement also has application with prostheses where more than one coil is required to transmit to at least one internal coil. The invention is also useful where it is necessary to couple power and/or information between electronic devices through a wall or membrane, such as in chemical engineering processes.

Modifications and adaptions may be made to the above described embodiments without departing from the spirit and scope of this invention which includes every novel feature and combination of features disclosed herein.

We claim:

1. Apparatus for improving the coupling of an external inductive transmitting coil to an internal inductive receiving coil to transmit power and/or data to said receiving coil from said transmitting coil comprising:
    a coupling coil inductively coupled to said transmitting coil to increase the coupling between said transmitting coil and said receiving coil.

2. Apparatus in accordance with claim 1 in which said coupling coil is coplanar with said transmitting coil.

3. Apparatus in accordance with claim 1 in which said coupling coil is concentric with said transmitting coil.

4. Apparatus in accordance with claim 3 in which said coupling coil is disposed outside said transmitting coil.

5. Apparatus in accordance with claim 3 in which said coupling coil is disposed inside said transmitting coil.

6. Apparatus in accordance with claim 1 including capacitance means connected to each of said transmitting coil and said coupling coil to form LC circuits therewith.

* * * * *